United States Patent [19]

Ranford

[11] Patent Number: 4,994,045
[45] Date of Patent: Feb. 19, 1991

[54] SPLIT SLEEVE SAFETY SYRINGE
[75] Inventor: Alan B. Ranford, Creve Coeur, Mo.
[73] Assignee: Sherwood Medical Company, St. Louis, Mo.
[21] Appl. No.: 511,667
[22] Filed: Apr. 20, 1990
[51] Int. Cl.$^5$ .............................................. A61M 5/32
[52] U.S. Cl. .................................... 604/198; 604/263
[58] Field of Search ............... 604/198, 192, 187, 110, 604/263

[56]  References Cited

U.S. PATENT DOCUMENTS

| | | | |
|---|---|---|---|
| 2,571,653 | 10/1951 | Bastien | 604/198 X |
| 3,780,734 | 12/1973 | Wulff | 604/198 X |
| 3,890,071 | 6/1975 | Leeson et al. | 604/198 X |
| 4,139,009 | 2/1979 | Alvarez | 604/198 X |
| 4,356,822 | 11/1982 | Winstead-Hall | 604/192 X |
| 4,425,120 | 1/1984 | Sampson et al. | 604/198 |
| 4,573,976 | 3/1986 | Sampson et al. | 604/198 |
| 4,631,057 | 12/1986 | Mitchell | 604/198 |
| 4,643,199 | 2/1987 | Jennings, Jr. et al. | 604/110 X |
| 4,643,200 | 2/1987 | Jennings, Jr. | 604/198 X |
| 4,650,468 | 3/1987 | Jennings, Jr. | 604/110 |
| 4,655,751 | 4/1987 | Harbaugh | 604/198 |
| 4,666,435 | 5/1987 | Braginetz | 604/198 |
| 4,681,567 | 7/1987 | Masters et al. | 604/198 |
| 4,693,708 | 9/1987 | Wanderer et al. | 604/198 |
| 4,695,274 | 9/1987 | Fox | 604/198 |
| 4,723,943 | 2/1988 | Spencer | 604/198 |
| 4,737,144 | 4/1988 | Choksi | 604/198 |
| 4,743,233 | 5/1988 | Schneider | 604/192 |
| 4,842,587 | 6/1989 | Poncy | 604/192 X |
| 4,874,383 | 10/1989 | McNaughton | 604/198 X |
| 4,927,417 | 5/1990 | Moncada et al. | 604/198 |

FOREIGN PATENT DOCUMENTS

| | | |
|---|---|---|
| A1216460 | 4/1987 | European Pat. Off. |
| A2240987 | 6/1987 | European Pat. Off. |
| A1250104 | 12/1987 | European Pat. Off. |
| A2252644 | 1/1988 | European Pat. Off. |
| 2833804 | 3/1979 | Fed. Rep. of Germany |
| 8606355 | 10/1986 | Fed. Rep. of Germany |
| 3609516 | 6/1987 | Fed. Rep. of Germany |

*Primary Examiner*—John D. Yasko
*Attorney, Agent, or Firm*—Andrew J. Beck; Montgomery W. Smith; Richard D. Allison

[57]  ABSTRACT

A safety syringe including a conventional syringe, a locating ring and an elongate and tubular sleeve wherein the locating ring includes an outwardly extending projecting tab thereon which extends outwardly from the distal end of the syringe to engage an elongate slot having closed distal and proximal ends on the elongate sleeve to allow the sleeve to be movable between a retracted position wherein a needle on the syringe is exposed and a pair of extended positions wherein the needle is enclosed by the sleeve. The sleeve is releasably retained in one of the extended positions and irreversibly retained in the other extended position upon rotational movement of the projecting tab into one or the other of a pair of perpendicular slots on the sleeve.

20 Claims, 2 Drawing Sheets

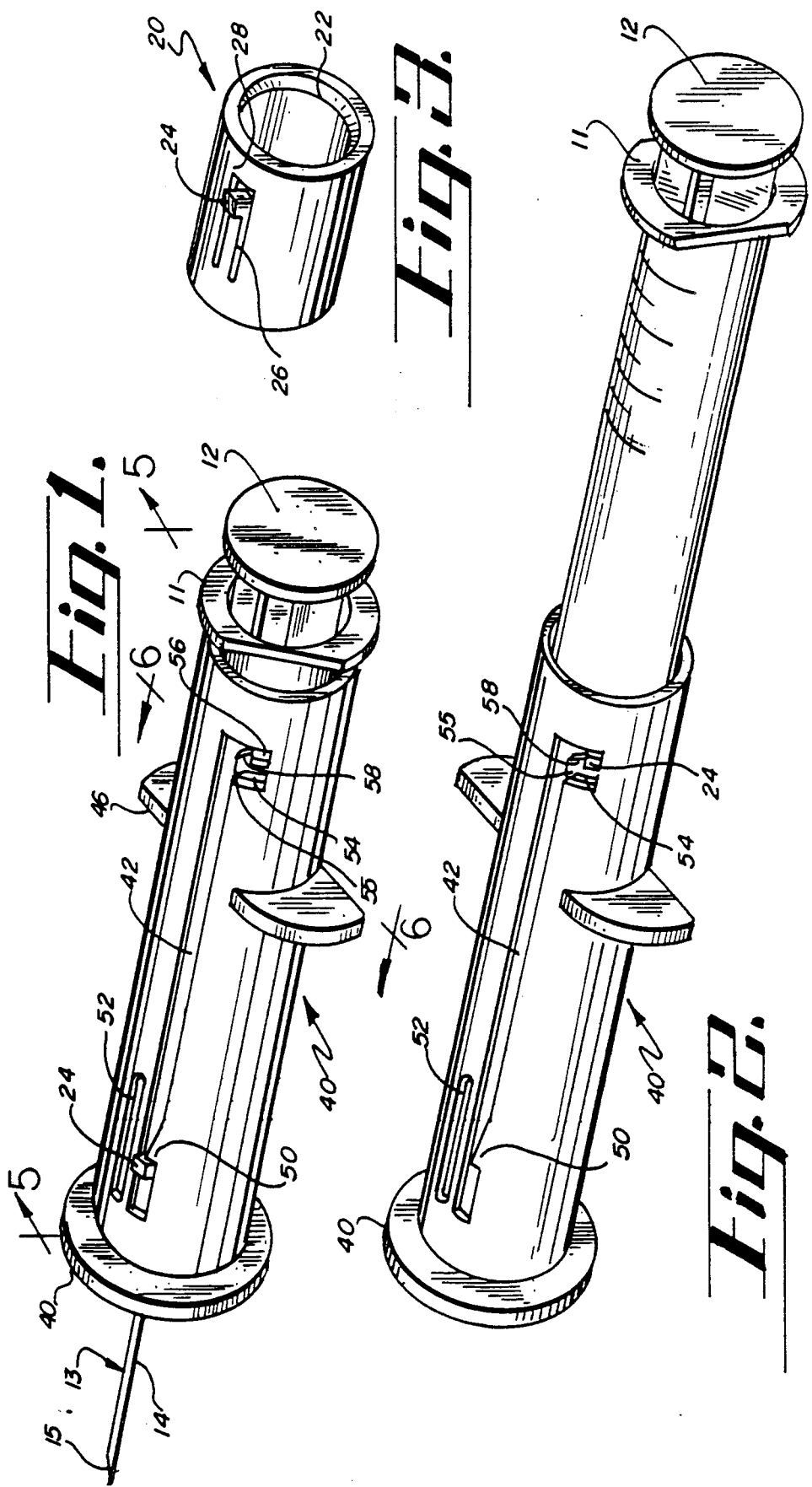

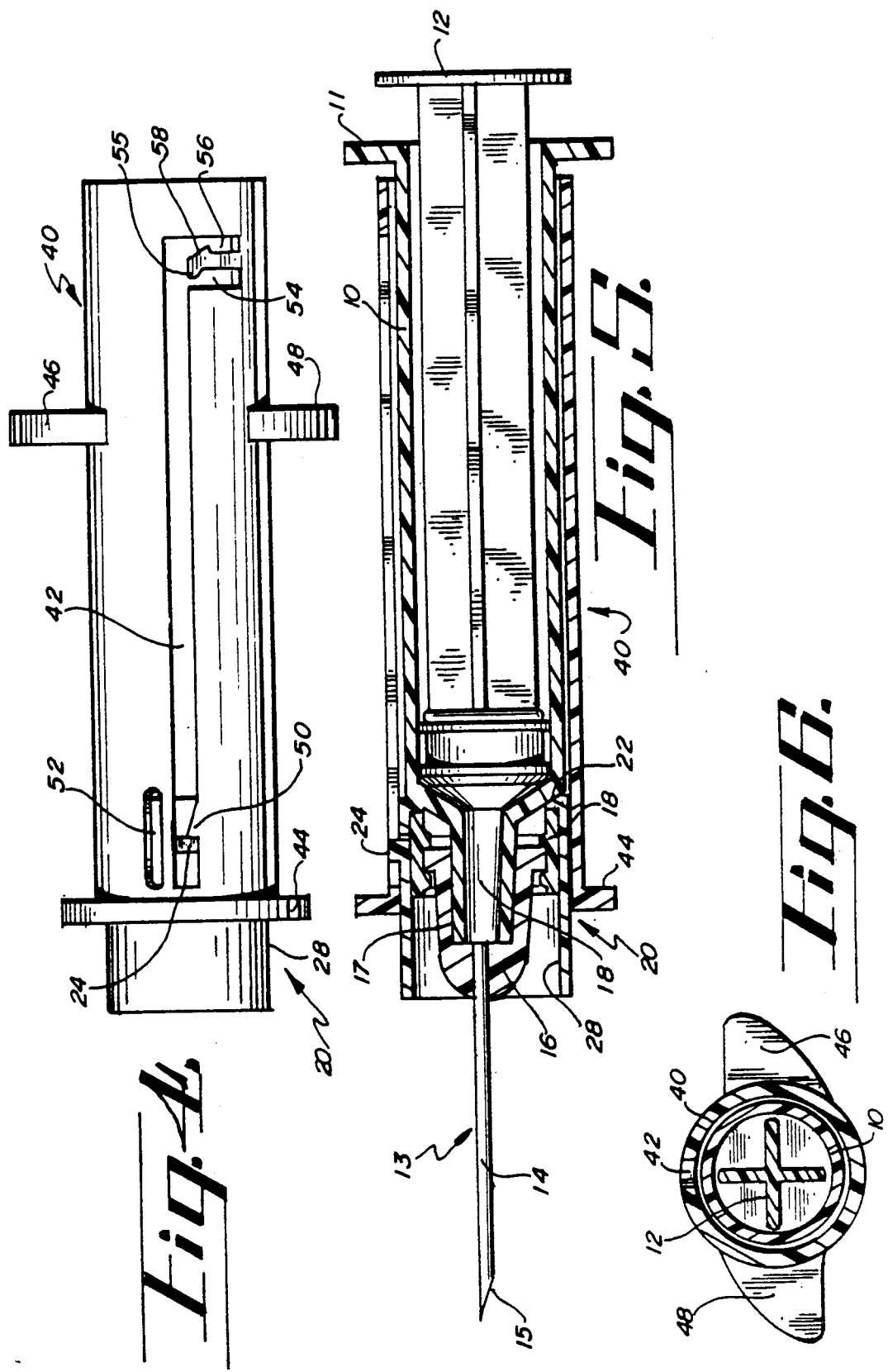

SPLIT SLEEVE SAFETY SYRINGE

FIELD OF THE INVENTION

This invention relates to syringes and more particularly to a safety type of syringe having a locating ring and a movable protective sleeve thereon. The present invention relates generally to my copending patent application entitled "Double Sleeve Safety Syringe" filed on July 25, 1989 assigned Ser. No. 07/385,343 which is incorporated herein by reference and commonly assigned to Sherwood Medical Company.

BACKGROUND OF THE INVENTION

The majority of syringes and needles used today for medical or laboratory purposes are intended to be discarded after a single use. Disposal of the syringes and needles poses a potential hazard for the individuals who use the syringes, as well as for those people who dispose of them. With the increased awareness concerning the potential for the transmission of AIDS and other infectious diseases, a number of different protective devices have been proposed to protect the user against accidental needle sticks. Protective devices of this type for use on syringes have become known generally in the medical field as safety syringes.

A number of safety syringe constructions have been proposed which satisfy the general requirement that the point of the needle be enclosed or covered once the syringe has been used. One common feature of these safety syringes is to provide a protective sleeve which is movable between a retracted position in which the needle point is exposed and an extended position in which the needle point is protected. In many of these safety syringes, the protective sleeve includes an elongate slot which extends lengthwise along the side of the protective sleeve and is open at the distal end of the protective sleeve. Although this type of safety syringe allows the user to lock the protective sleeve in the extended position, the locking mechanism may be readily defeated by prying open the distal end of the protective sleeve to defeat the locking mechanism. Other safety syringes include protective sleeves having relatively complex twist-to-lock mechanisms and which do not readily indicate when the protective sleeve has been locked in the extended position. In other safety syringes, the protective sleeve locks automatically when the sleeve is extended. This automatic locking of the protective sleeve may result in the accidental locking of the protective sleeve in the extended position prior to the use of the syringe.

Although many of the above described devices meet the general requirements for a safety syringe, many of the proposed designs are not commercially viable because they are much too complicated to manufacture economically and efficiently. Additionally, other devices would require a modification in the conventional method of using a syringe. This is generally unacceptable due to the large amount of time and expense involved in teaching all of the potential users of such a device the proper technique in using the new device.

Therefore, it is apparent that a need remains for a safety type of syringe having a protective sleeve which will not interfere with the conventional method of using the syringe and which may be produced efficiently and economically.

SUMMARY OF THE PRESENT INVENTION

An object of the present invention is to substantially overcome the disadvantages mentioned above.

Another object of the present invention is to provide a safety syringe which performs all of the general requirements of this type of syringe and which can not be readily manipulated to defeat the locking mechanism once the protective sleeve is placed in a readily observable locked and extended position.

A further object of the present invention is to provide a safety syringe which includes a protective sleeve which is movable between a releasable extended position and a locked and extended position.

The present invention consists generally of a locating ring mounted on the distal end of a conventional syringe which cooperates with a protective sleeve slidably positioned along the outer surface of the syringe barrel. The protective sleeve is initially maintained in a releasable retracted position wherein the protective sleeve is adjacent to the syringe barrel and the needle point is exposed. From the retracted position, the protective sleeve is slidable to a pair of extended positions wherein the protective sleeve extends beyond the distal needle point to protect the user from accidental contact with the needle point.

The locating ring of the present invention includes an outwardly directed projecting tab member which extends outwardly from the locating ring and is adapted to be received in an elongate slot located along the side of the protective sleeve. The elongate slot extends between the closed proximal end and the closed distal end of the protective sleeve. A retaining lip is positioned along the elongate slot to extend inwardly into the elongate slot and releasably retain the tab member near the distal end of the elongate slot when the protective sleeve is moved to the retracted position.

A pair of perpendicularly oriented slots are located near the proximal end of the elongated slot. The first perpendicular slot is located proximal to the second perpendicular slot along the elongate slot and includes a locking lip therein to irreversibly retain the protective sleeve in an extended and locked position once the syringe has been used. The second perpendicular slot includes a detent therein to temporarily retain the protective sleeve in a releasable extended position which temporarily protects the needle point. The releasable extended position is particularly useful in situations where the syringe is filled with medication at one location and then transported to a second location where the medication is dispensed form the syringe. The releasable extended position provides the user with needed protection against accidental contact with the needle point during the transport of the medication-containing syringe and allows the user to return the protective sleeve to the retracted position to dispense the medication from the syringe.

An advantage of the present invention is that the safety syringe is simple to operate and allows the user to slide the protective sleeve between a releasable retracted position and a pair of extended positions.

A further advantage of the present invention is that the distal end of the protective sleeve is closed to prevent the protective sleeve from being pried open and returned to the retracted position.

Yet another advantage of the present invention is that the protective sleeve is rotatable to a temporary or releasable extended position wherein the protective sleeve is retained in the extended position until the protective sleeve is rotated to move the tab member from the second perpendicular slot.

Yet another advantage of the present invention is that the protective sleeve is initially movable to a releasable retracted position wherein the protective sleeve is retained substantially adjacent to the barrel of the syringe so that the safety syringe may be used in a conventional manner.

BRIEF DESCRIPTION OF THE DRAWINGS

FIG. 1 is an elevated perspective view of the present invention with the protective sleeve in the retracted position;

FIG. 2 is an elevated perspective view of the present invention with the protective sleeve in the extended and locked position;

FIG. 3 is an elevated perspective view of the locating ring of the present invention;

FIG. 4 is an elevated side view of the present invention showing the protective sleeve and locating ring in the partially assembled condition;

FIG. 5 is a side view partially in cross-section of the present invention taken generally along lines 5—5 of FIG. 1; and FIG. 6 is a cross-sectional view of the present invention taken generally along lines 6—6 of FIG. 1.

DETAILED DESCRIPTION OF THE PREFERRED EMBODIMENT

As described herein, the present invention is intended to be used in conjunction with a conventional syringe; however, the protective sleeve and locating ring of the present invention are readily adaptable for use on nearly any medical or laboratory device having an elongate barrel section and a needle. For example, the present invention may be adapted for use on commonly available medical devices preferably having a luer lock or other projection on the distal end thereof. Accordingly, as used herein, the term "syringe" is intended to broadly include or encompass nearly any medical or scientific device having a needle extending therefrom wherein it is desired to protect a user from accidental contact with the needle point.

In describing the present invention, the term "distal end" is used herein to refer to the end of the part closest to the normally exposed needle point. The term "proximal end" is used herein to refer to the end of the part farthest from the normally exposed needle point. The term "retracted position" is used herein to refer to the relative position of the protective sleeve about the syringe barrel wherein the proximal end of the protective sleeve is adjacent to the proximal end of the syringe barrel and the distal needle point is exposed. The term "extended position" is used herein to refer to the relative position of the protective sleeve wherein the proximal end of the protective sleeve is adjacent to the distal end of the syringe barrel and the distal end of the protective sleeve extends beyond the distal needle point.

The present invention is described herein with particular reference to a conventional syringe having an elongate and tubular syringe barrel section 10 with a proximally located finger flange 11; a plunger member 12 which is slidable within the barrel section 10, and an elongate and hollow needle assembly 13 through which the contents of the barrel section 10 are dispensed when the plunger member 12 is moved distally in the barrel section 10. The needle assembly 13 includes an elongate and hollow needle 14 having a sharpened needle point 15 at the distal end thereof and an enlarged hub member 16 at the proximal end of the needle assembly 13.

A conically-shaped luer tip 17 and a cylindrically-shaped luer lock skirt 18 are integrally formed on the distal end of the barrel section 10 and are arranged thereon such that the luer lock skirt 18 is spaced apart from and encircles the luer tip 17. The interior surface of the luer lock skirt 18 preferably includes internally oriented threads which are adapted to threadedly engage complimentary ridges on the proximal end of the needle hub 16 to releasably retain the needle assembly 13 in fluid-tight communication with the distal end of the barrel section 10. The exterior surface of the luer lock skirt 18 is generally cylindrical and extends parallel to the longitudinal axis of the barrel section 10.

As illustrated in the drawings, the preferred embodiment of the present invention consists generally of a cylindrical locating ring 20 which is fixedly attached to the luer lock skirt 18 on the distal end of the barrel section 10 and an elongate and tubular protective sleeve 40 which is slidably movable over the locating ring 20 and the barrel section 10. The locating ring 20 of the present invention is preferably constructed of a rigid plastic such as a polycarbonate and is press-fit or fused to the external surface of the luer lock skirt 18. The protective sleeve 40 slidably fits over the syringe barrel 10 and locating ring 20 and is movable between retracted and extended positions as described hereinafter.

As illustrated in FIG. 5, the internal diameter of the locating ring 20 is approximately equal to the external diameter of the luer lock skirt 18 and preferably includes an inwardly directed retaining ridge 22 adjacent to the internal surface of the proximal end of the locating ring 20. The retaining ridge 22 is adapted to engage and fixedly retain the locating ring 20 on the luer lock skirt 18 adjacent to the distal end of the barrel section 10. The external surface of the locating ring 20 generally includes a circumferential body section 28 and an outwardly directed projecting tab member 24. The tab member 24 extends outwardly from the proximal side of the body section 28 a sufficient distance to cooperate with an elongate slot 42 which extends longitudinally along one side of the protective sleeve 40 as described hereinafter. As best illustrated in FIG. 3, the tab member 24 is generally bordered by a slot 26 which allows the tab member 24 to be depressed with respect to the body section 28 of the locating ring 20 during the assembly of the safety syringe of the present invention as described hereinafter. Once the syringe of the present invention is assembled, the tab member 24 is prevented from being depressed by contact between the external surface of the luer lock skirt 18 and the internal surface of the tab member 24.

The protective sleeve 40 of the present invention is a generally elongate and tubular sleeve member which is preferably constructed of a semi-rigid plastic such as polypropylene. One side of the protective sleeve 40 includes the elongate slot 42 extending longitudinally between the proximal and distal ends thereof. An outwardly extending circumferential flange member 44 is located on the distal end of the protective sleeve 40. A pair of outwardly directed wing-shaped finger flanges 46 extend outwardly from the protective sleeve 40. The finger flanges 46 are oriented perpendicular to the longitudinal dimension of the protective sleeve 40 near the proximal end of the protective sleeve 40. The flange member 44 and the finger flanges 46 enable the user to safely and conveniently slide and rotate the protective sleeve 40 about the barrel section 10 of the syringe between the retracted and extended positions as described hereinafter.

The elongate slot 42 of the present invention preferably includes distal and proximal ends and extends lengthwise along the side of the protective sleeve 40 to a position adjacent to the distal and proximal ends of the protective sleeve 40. A wedge-shaped retaining lip 50 projects inwardly into the elongate slot 42 near the distal end of the elongate slot 42 to retain the tab member 24 distally of the retaining lip 50 in the elongate slot 42 when the protective sleeve 40 is in the retracted position as described hereinafter. The protective sleeve 40 also includes an expansion channel 52 which is oriented parallel to the elongate slot 42 near the distal end thereof and adjacent to the retaining lip 50 to enable the tab member 24 to be releasably moved beyond the retaining lip 50 to allow the protective sleeve 40 to be moved from the retracted position to one of the extended positions as described more fully hereinafter.

As illustrated in FIG. 4, first and second perpendicular slots, 56 and 54 respectively, are located near the proximal end of the elongate slot 42 to selectively retain the tab member 24 therein when the protective sleeve 40 is moved to one of the extended positions as described hereinafter. The first perpendicular slot 56 is oriented perpendicular to the elongate slot 42 and consists of a generally rectangularly-shaped opening in the protective sleeve 40 which is located adjacent to the proximal end of the elongate slot 42. The first perpendicular slot 56 includes an inwardly projecting and wedge-shaped locking ridge 58 which preferably projects from the distal side of the first perpendicular slot 56 into the first perpendicular slot 56 to enable the user to move the protective sleeve 40 to a locked and extended position by initially pushing the protective sleeve 40 distally until the tab member 24 is adjacent to the first perpendicular slot 56 and then rotating the protective sleeve 40 counterclockwise about the barrel section 10 until the tab member 24 is permanently received in the first perpendicular slot 56. The second perpendicular slot 54 is located distally to the first perpendicular slot 56 along the elongate slot 42 and consists of a generally rectangularly-shaped opening in the protective sleeve 40 having a detent 55 which extends inwardly from the proximal side of the second perpendicular slot 54 adjacent to the elongate slot 42. The second perpendicular slot 54 is oriented perpendicular to the elongate slot 42 to enable the user to move the protective sleeve 40 to a releasable and extended position by initially pushing the protective sleeve 40 distally until the tab member 24 is adjacent to the second perpendicular slot 54 and then rotating the protective sleeve 40 counterclockwise about the barrel section 10 until the tab member 24 is received in the second perpendicular slot 56.

It should be understood that although the first perpendicular slot 56 and the second perpendicular slot 54 are described and illustrated herein as being positioned on the same side of the elongate slot 42 and adjacent to one another, it is anticipated that their relative positions or shape may be modified without departing from the scope of the present invention. For example, it is anticipated that the first perpendicular slot 56 and the second perpendicular slot 54 may be located on opposite sides of the elongate slot 42 so that rotation of the protective sleeve 40 in one direction will move the tab member 24 into the first perpendicular slot 56 and rotation of the protective sleeve 40 in the other direction will move the tab member 24 into the second perpendicular slot 54.

The present invention is assembled by depressing the tab member 24 on the locating ring 20 until the external surface of the tab member 24 adjacent to body section 28 of the locating ring 20 and then sliding the locating ring 20 through the distal end of the protective sleeve 40 so that the tab member 24 is aligned with the elongate slot 42. A conventional syringe, as described above, is then attached to the assembled locating ring 20 and protective sleeve 40 (FIG. 4) by sliding the syringe through the proximal end of the protective sleeve 40 until the retaining ridge 22 on the internal surface of the locating ring 20 engages and partially deforms the external surface of the luer lock skirt 18 on the distal end of the barrel section 10. The contact between the internal surface of the locating ring 20 and the external surface of the luer lock skirt 18 prevents the tab member 24 from being depressed once the locating ring 20 has been placed on the luer lock skirt 18 so that the tab member 24 is retained within the elongate slot 42 of the protective sleeve 40 and cannot be removed therefrom unless excessive force is used to disassemble the present invention.

Once the safety syringe of the present invention is assembled, the user may move protective sleeve 40 proximally along the barrel section 10 to a retracted position wherein the distal end of the protective sleeve 40 is adjacent to the distal end of the luer tip 17. The needle assembly 13 may then be attached to the present invention in a conventional manner by grasping the finger flanges 46 on the protective sleeve 40 and then threadedly engaging the complementary ridges on the needle hub 16 with the internal threads on the luer lock skirt 18. As illustrated in FIG. 1, when the protective sleeve 40 is in the retracted position, the needle point 15 and nearly the entire length of the shaft of the hollow needle 14 extend distally beyond the distal end of the protective sleeve 40 and medication may be drawn into the present invention in a conventional manner.

The protective sleeve 40 is releasably held in the retracted position by contact between the tab member 24 and the inwardly directed retaining lip 50 in the elongate slot 42. The retaining lip 50 cooperates with the tab member 24 to prevent the protective sleeve 40 from moving distally along the barrel section 10. Additionally, the longitudinal orientation of the elongate slot 42 enables the user to attach the needle assembly 13 to the luer tip 17 while grasping only the finger flanges 46 of the protective sleeve 40 because the engagement between the tab member 24 and the elongate slot 42 and the engagement between the locating ring 20 and the luer lock skirt 18 prevents rotation of the protective sleeve 40 about the barrel section 10.

In order for the user to move the protective sleeve 40 from the retracted position to one of the extended positions, the user must grasp the finger flanges 46 along the proximal end of the protective sleeve 40 and slightly rotate the protective sleeve 40 clockwise about the syringe barrel 10. This clockwise rotation of the protective sleeve 40 about the barrel section 10 causes the tab member 24 to press against the side of the elongate slot 42 adjacent to the expansion channel 52 and compress the expansion channel 52. Compression of the expansion channel 52 enables the tab member 24 to pass beyond the retaining lip 50 as the user pushes the protective sleeve 40 distally along the barrel section 10. Further distal movement of the protective sleeve 40 along the barrel section 10 allows the protective sleeve 40 to be moved to one of the extended positions wherein the shaft of the needle 14 and the needle point 15 are protected by the protective sleeve 40 and tab member 24 is moved adjacent to either the first or second perpendicular slot, 56 or 54, respectively, near the proximal end of the elongate slot 42.

As the protective sleeve 40 is released from the retracted position and moved distally along the barrel section 10, the protective sleeve 40 may be moved to an initial releasable and extended position The user may move the protective sleeve 40 to the releasable and extended position by moving the protective sleeve 40 distally along the syringe barrel 10 until the tab member 24 is adjacent to the second perpendicular slot 54. The protective sleeve may then be rotated counterclockwise by grasping the finger flanges 46 and rotating the protective sleeve 40 about the barrel section 10 to cause the tab member 24 to pass beyond the detent 55 and enter the second perpendicular slot 54. In this position, the protective sleeve cannot be retracted unless the protective sleeve 40 is rotated clockwise about the barrel section 10 to move the tab member 24 past the detent 55 and into the elongate slot 42.

Once the tab member 24 is removed from the second perpendicular slot 54, the protective sleeve 40 may be moved proximally along the barrel section 10 and returned to the retracted position so that the user may administer the medication contained therein in a conventional manner. Once the injection has been given, the protective sleeve 40 may be moved to a locked and extended position (FIG. 2) by moving the protective sleeve 40 distally along the barrel section 10 until the tab member 24 contacts the proximal end of the elongate slot 42. The user may then rotate the protective sleeve 40 counterclockwise about the barrel section 10 so that the tab member 24 enters the first perpendicular slot 56. The rotation of the protective sleeve 40 about the barrel section 10 causes the tab member 24 to pass beyond the locking lip 58 of the first perpendicular slot 56 so that the protective sleeve 40 is in an extended and locked position. Once this occurs, the protective sleeve 40 can no longer be rotated or moved about the barrel section 10 unless extraordinary force is used to force the tab member 24 beyond the locking lip 58 of the first perpendicular slot 56 and into the elongate slot 42.

The foregoing description of the preferred embodiment is intended to be illustrative of one form of the invention and may be modified without departing from the scope of the present invention which is defined by the claims attached hereto.

What is claimed is:

1. A medical device, comprising
 a syringe means having proximal and distal ends and a generally elongate barrel section extending therebetween,
 an elongate and hollow needle having a distal needle point thereon operatively connected to said distal end of said barrel section,
 a locating ring operatively connected to said distal end of said barrel section and including a body section and an outwardly extending tab member extending from said body section of said locating ring,
 an elongate sleeve member having circumferentially closed proximal and distal ends, said sleeve member adapted to be longitudinally movable over said barrel section and said locating ring between a retracted position wherein said needle point is exposed and an extended position wherein said sleeve member protects said needle point,
 said sleeve member including an elongate slot having proximal and distal ends, said elongate slot extending between said proximal and distal ends of said sleeve member and wherein said tab member of said locating ring extends therein to slidably retain said sleeve member about said barrel section and said locating ring, and
 a first perpendicular slot located near the proximal end of said elongate slot and said first perpendicular slot is adapted to receive said tab member therein and retain said sleeve member in said extended position wherein said needle point is protected when said sleeve member is rotated about said barrel section.

2. The medical device of claim 1, wherein said proximal and distal ends of said elongate slot are adjacent to said proximal and distal ends of said sleeve member and wherein said first perpendicular slot includes a locking means associated therewith to retain said sleeve member in an extended and locked position.

3. The medical device of claim 2, wherein a second perpendicular slot is located near said proximal end of said elongate slot and includes a detent extending therein to enable said sleeve member to be retained in a releasable and extended position by rotating said sleeve member about said barrel section to move said tab means into said second perpendicular slot.

4. The medical device of claim 1, wherein a retaining ridge is operatively associated with said elongate slot to releasably contact said tab member and retain said sleeve member in said retracted position.

5. The medical device of claim 4, wherein an expansion channel is oriented parallel to said elongate slot and adjacent to said retaining ridge slot to enable said sleeve member to be releasably movable from said retracted position to said extended position upon rotation of said sleeve member about said barrel section.

6. The medical device of claim 1, wherein said tab member on said locating ring may be depressed with respect to said body section of said locating ring to facilitate the assembly of said sleeve member and said syringe means.

7. The medical device of claim 6, wherein said tab member is depressed to a position adjacent to the outer surface of said body section of said locating ring to allow said tab member to be inserted into said elongate slot on said sleeve member.

8. A safety syringe, comprising:
 a syringe having proximal and distal ends and a generally elongate barrel section extending therebetween,
 an elongate and hollow needle having a distal needle point thereon operatively connected to said distal end of said barrel section,
 a locating ring having a body section and tab means thereon, said locating ring being operatively connected to said distal end of said barrel section and wherein said tab means extends radially outwardly from said body section of said locating ring,
 an elongate and tubular sleeve member having proximal and distal ends, said sleeve member being adapted to be longitudinally movable over said barrel section and said locating ring between a retracted position wherein said sleeve member is adjacent to said barrel section and an extended position wherein said sleeve member protects said needle point, an elongate slot longitudinally oriented along said sleeve member, said slot extending between said proximal and distal ends of said sleeve member and being adapted to slidably receive said tab means therein, said elongate slot having a proximal end located distal to said proximal end of said sleeve member and a distal end located proximal to said distal end of said sleeve member, a retaining ridge adapted to extend into said elongate slot near said distal end thereof to releasably contact said tab means and retain said sleeve member in said retracted position, and an expansion slot adjacent to said retaining ridge to enable said sleeve member to be rotated about said barrel section so that said tab means slidably passes beyond said retaining ridge as said sleeve member is moved from said retracted position to said extended position 9. The safety syringe of claim 8, wherein a first perpendicular slot is located near said proximal end of said elongate slot, said first perpendicular slot being adapted to receive said tab means therein when said sleeve member moved to said extended position.

10. The safety syringe of claim 8, wherein first and second perpendicular slots are located near said proximal end of said elongate slot, said first and second perpendicular slots being adapted to receive said tab means therein and wherein said first perpendicular slot includes a locking means associated therewith to retain said projecting tab therein and retain said sleeve member in an extended and locked position wherein said needle point is protected.

11. The safety syringe of claim 10, wherein said second perpendicular slot includes a detent therein and is located proximal to said first perpendicular slot along said elongate slot and wherein said second perpendicular slot is adapted to releasably receive said tab means therein to retain sleeve member in a releasable and extended position wherein said needle point is temporarily protected.

12. A safety syringe comprising
a tubular member having proximal and distal ends and a generally elongate barrel section extending therebetween, an elongate and hollow needle having a distal needle point thereon said needle being adapted to be operatively connected to said distal end of said barrel section, a cylindrical skirt member extending distally from said distal end of said barrel section, said skirt member being adapted to receive a portion of said needle therein, a locating ring including a body section having an outer surface and an outwardly extending projecting member extending therefrom, said locating ring being operatively connected to said skirt member on said distal end of said barrel section, an elongate and tubular sleeve member having proximal and distal ends, said sleeve member being adapted to be longitudinally slidable over said barrel section and said locating ring between a retracted position wherein said sleeve member is adjacent to said barrel section and said locating ring so that said needle point is exposed and an extended position wherein said sleeve member protects said needle point, an elongate slot extending lengthwise along said sleeve member and including proximal and distal ends positioned near said proximal and distal ends of said sleeve member and wherein said projecting member is adjacent to said distal end of said elongate slot when said sleeve member is in said retracted position and adjacent to said proximal end of said elongate slot when said sleeve member is in said extended position, and a first perpendicular slot located near said proximal end of said elongate slot and said first perpendicular slots being adapted to receive said projecting member therein upon rotational movement of said sleeve member about said barrel section.

13. The safety syringe of claim 12, wherein a retaining ridge projects inwardly into said elongate slot near said distal end of said elongate slot and wherein an expansion slot is positioned parallel to said elongate slot near said retaining ridge to allow said projecting member to move from said proximal end of said elongate slot to said distal end of said elongate slot such that said sleeve member is releasably movable from said retracted position to said extended position upon rotational movement of said sleeve member about said barrel section.

14. The safety syringe of claim 12, wherein said first perpendicular slot is located adjacent said proximal end of said elongate slot and includes a locking means operatively associated therewith to retain said projecting member in said first perpendicular slot such that said sleeve member is longitudinally movable and rotatable to an extended and locked position wherein said needle point is protected.

15. The safety syringe of claim 14, wherein a second perpendicular slot is located along said elongate slot distal to said first perpendicular slot, said second perpendicular slot includes a detent extending therein and is adapted to receive said projecting member therein such that said sleeve member is rotatable to an extended and releasable position wherein said needle point is protected.

16. A safety syringe comprising
a syringe member having proximal and distal ends, a generally elongate and tubular barrel section therebetween and a longitudinally slidable plunger means therein, an elongate and hollow needle member having a needle hub and a distal needle point thereon, said needle hub being adapted to be operatively connected to said distal end of said barrel section, a cylindrical locating ring having a body section and a radially outwardly extending projecting tab thereon, said locating ring being adapted to be fixedly mounted on said distal end of said syringe member and adjacent said needle hub, an elongate and tubular sleeve member having proximal and distal ends thereon, said sleeve member being adapted to be longitudinally slidable over said barrel section and said locating ring between a needle point exposing retracted position and first and second extended positions wherein said needle point is protected, an elongate and generally rectangularly-shaped slot means extending lengthwise along said sleeve member, said slot means including a distal end located proximally of said distal end of said sleeve member and a proximal end located distally of said proximal end of said sleeve member wherein said projecting member is movable between said distal and proximal ends of said slot means as said sleeve member is moved between said retracted and extended positions, a generally wedge-shaped retaining ridge extending into said slot means near the distal end thereof, an expansion slot oriented generally parallel to said slot means and adjacent to said retaining ridge wherein said retaining ridge and said expansion slot cooperate to releasably retain said projecting tab distally of said retaining ridge when said sleeve member is in said retraced position, first and second perpendicular slots operatively located near said proximal end of said slot means, said first and second perpendicular slots being oriented generally parallel to each other and adapted to receive said projecting means therein upon rotational movement of said sleeve member about said barrel section when said sleeve member is moved to said first and second extended positions, and a locking means operatively positioned in one of said first and second perpendicular slots to irreversibly retain said projecting means in one of said first and second perpendicular slots when said sleeve member is in said second extended position.

17. The safety syringe of claim 16, wherein said locking means is in said first perpendicular slot and wherein said first and second perpendicular slots are oriented generally perpendicular to said slot means to receive said projecting means therein upon rotational movement of said sleeve member about said barrel section and wherein said sleeve member is releasably retained in said first extended position upon rotational movement of said projecting means into said second perpendicular slot.

18. The safety syringe of claim 16 wherein said sleeve member is releasable from said retracted position upon rotational movement of said sleeve member about said barrel section.

19. A method of assembling a safety syringe comprising the steps of inserting a locating ring having a depressible outwardly extending projecting means thereon into an elongate and cylindrical sleeve member by depressing the projecting means until the projecting means on the locating ring is aligned with an elongate slot having closed distal and proximal ends on the sleeve member, releasing the projecting means so that the projecting means is slidably retained within the distal and proximal ends of the elongate slot, and sliding the proximal end of the sleeve member over the distal end of a syringe barrel until the inner surface of the locating ring contacts and operationally engages a luer skirt on the distal end of the syringe barrel.

20. The method of claim 19, wherein a sheathed needle is then attachable to the distal end of the syringe barrel and wherein the outer surface of the luer skirt prevents the projecting means from being depressed once the locating ring engages the luer skirt.

* * * * *